United States Patent [19]

Weber et al.

[11] Patent Number: 4,862,887
[45] Date of Patent: Sep. 5, 1989

[54] HEART CATHETER

[75] Inventors: Helmut Weber, Neuried; Eberhard Unsoeld, Oberschleissheim; Heinz Ruesch, Waiblingen; Klaus Schmitt, Remshalden-Grunbach, all of Fed. Rep. of Germany

[73] Assignee: Gesellschaft fuer Strahlen und Umweltforschung (GSF), Neuherberg, Fed. Rep. of Germany

[21] Appl. No.: 199,387

[22] Filed: May 27, 1988

[30] Foreign Application Priority Data

May 29, 1987 [DE] Fed. Rep. of Germany ....... 3718139

[51] Int. Cl.⁴ ............................................ A61B 17/36
[52] U.S. Cl. ................. 128/303.1; 128/786; 128/642; 128/734
[58] Field of Search ..................... 128/642, 303.1, 786, 128/785, 734, 395–398

[56] References Cited

U.S. PATENT DOCUMENTS

| 3,533,403 | 10/1970 | Woodson | 128/642 |
| 3,754,555 | 8/1973 | Schmitt | 128/785 |
| 4,249,533 | 2/1981 | Komiya | 128/321 |
| 4,421,382 | 12/1983 | Doi et al. | 128/303.1 |
| 4,519,390 | 5/1985 | Horne | 128/303.1 |
| 4,681,104 | 7/1987 | Edelman | 128/303.1 |

FOREIGN PATENT DOCUMENTS 2017506 10/1979 United Kingdom ............ 128/303.1

Primary Examiner—Max Hindenburg
Assistant Examiner—Scott Getzow
Attorney, Agent, or Firm—Klaus J. Bach

[57] ABSTRACT

In a heart catheter which consists of a hose having a sonde with an electrode structure for locating pathological areas arranged at its distal end, a light transmitting fiber is movably disposed in the hose and the hose has sensors associated therewith so as to be movable together with the fiber out of the distal end of the hose for engagement with the tissue of the pathological area for positioning the distal end of the hose at a predetermined distance and location relative to the pathological area in order to provide for appropriate irradiation of the pathological area by radiation energy supplied through the light transmitting fiber.

4 Claims, 1 Drawing Sheet

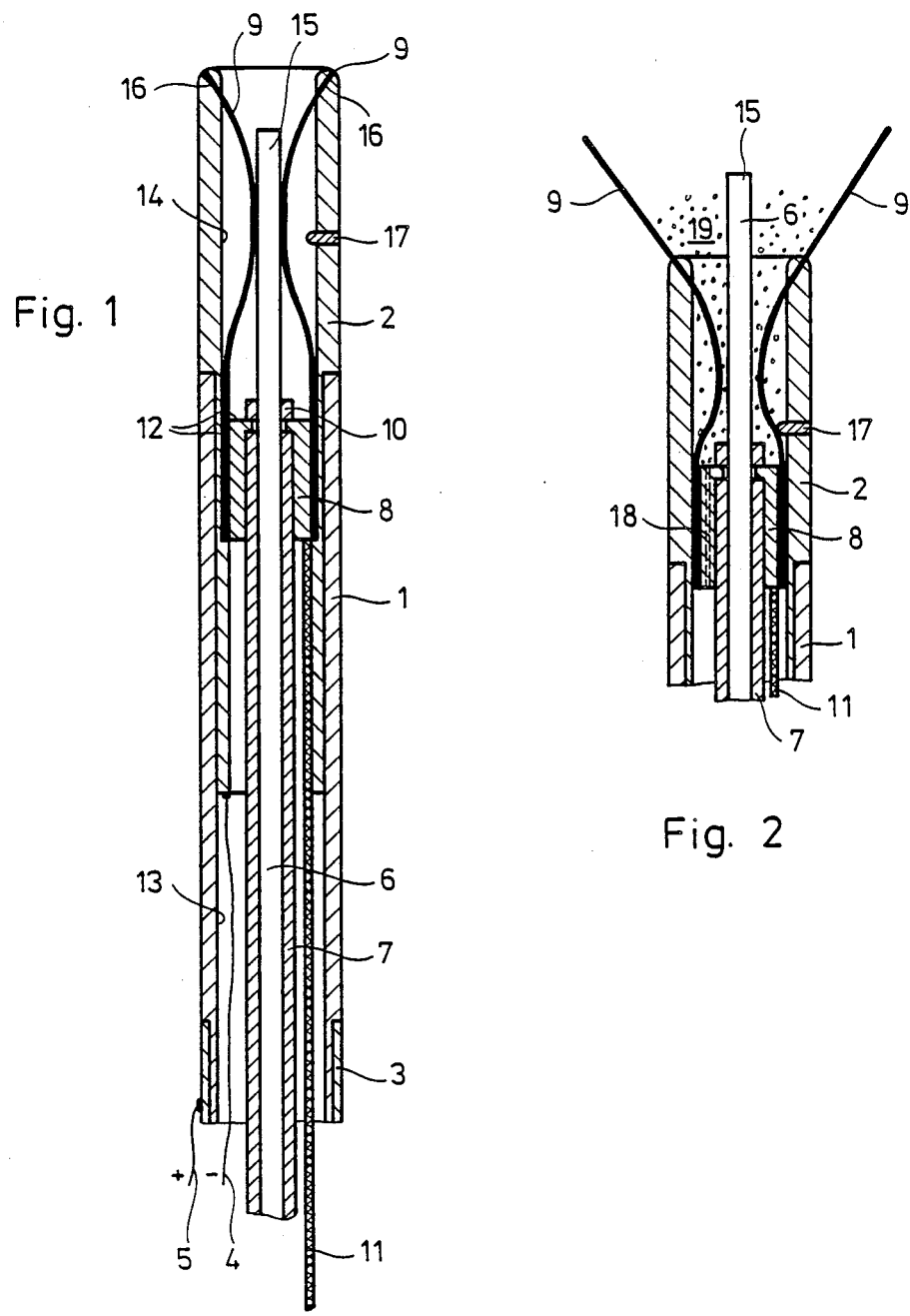

HEART CATHETER

BACKGROUND OF THE INVENTION

The invention relates to a heart catheter which consists of a hose having a free end formed as a sonde provided with an electrode arrangement for locating pathological areas.

A heart catheter is provided with a sonde tip in such a manner that subendocardial arrithmogenic areas can be located by means of electrodes associated with the sonde tip (Am. J. Cardial 1984; 54: 186–198). As a result of the movement of the heart however the position of the sonde tip does not remain well determined over an extended period of time so that correlation of diagnosis and subsequent catheter-based therapy is not certain.

There are also heart catheters which include in the catheter hose a light transmitting fiber that permits the execution of photoablations of heart tissue, though in a somewhat uncontrolled manner (Circulation 71, No. 3, 579-586, 1985). With such catheters it is possible that the light fibers come into contact with the endocardium and that they may cause a photodissection of the subendocardium and the myocardium or even a perforation of the heart walls. Even if the irradiation procedures performed by such catheters are supported by additional means such as a second observation catheter or by X-ray surveillance, utilization of such catheters is quite limited.

It is the object of the present invention to provide a heart catheter which permits the operator to locate a specific area of the heart interior and to provide for subsequent irradiation of this area during which the catheter tip is maintained in a stable position while the fiber end is not in contact with the endocardium.

SUMMARY OF THE INVENTION

This object is achieved by a heart catheter which consists of a hose having a sonde with an electrode structure for locating remote pathological areas arranged at its distal end and a light transmitting fiber movably disposed in the hose and having associated therewith sensors so as to be axially movable with the fiber out of the distal end of the hose in engagement with the tissue of the pathological area for appropriately positioning the end of the catheter and the light transmitting fiber relative to the pathological area for irradiation of the pathological area through the light transmitting fiber.

Means are provided for supplying a salt solution through the hose along the fiber to the area to be irradiated so as to generate a light transmissive, that is, blood-free, path for the irradiation energy from the fiber end to the pathological area.

Preferably the end of the fiber is supported in the end of the hose, i.e., the electrode structure by way of a piston-type slide member on which also the sensors are mounted and the sensors are prestressed so as to project forward outwardly when moved out of the front end of the hose or rather electrode for engagement with the tissue of the pathological area, the length of the sensors and their preset being so chosen that in the fully extended position the fiber end is disposed at a predetermined distance from the pathological area.

An accurately controlled percutaneous photocoagulation through the veins or arteries has so far not been possible. The methods known in the art do not permit accurate locating of the areas to be irradiated and furthermore there is always a possibility of heart perforation; accurate, stable positioning of the catheter tip is impossible. The catheter according to the present invention however permits irradiation of selected subendocardial zones without the quartz light fiber end coming into contact with the endocardium (the membrane lining the heart cavity) and without the possibility of dislocation of the catheter tip. It also avoids formation of blood clots during laser irradiation.

This is achieved by the distal electrode which is associated with the catheter and which includes a sensing structure providing for the controlled extension of the light transmitting fiber. With the given arrangement the catheter tip can be properly located relative to the endocardium while, at the same time, the fiber tip may be maintained at the necessary distance from the endocardium. Continuous introduction of a physiological salt solution through the catheter keeps the fiber surrounded by the salt solution and the blood at a distance from the fiber such that between the fiber tip and the heart membrane there is practically only salt solution which will not coagulate during laser irradiation and which is also laser light transmissive. The arrangement according to the invention has the material advantage that laser irradiation of areas of the inner heart membrane can be performed by catheter insertion, that is, in a percutaneous manner without a direct contact of the light fiber tip with the inner heart membrane and without the danger of dislocation of the catheter tip during the laser irradiation procedure. This is achieved mainly by the extendible sensors which are associated with the distal electrode and by the continuous flushing capabilities of the heart catheter system according to the invention.

Such as apparatus permits the treatment and correction of disorders of the heart rhythm without openheart surgery, without the chances of intracardial electroshock, without the danger of heart perforation and even without total anesthesia. Treatment with the apparatus according to the invention may well omit the requirement for life-long medication or the installation of expensive and unreliable heart pacers and consequently will result in a substantial improvement of the quality of life of a patient and it will furthermore result in substantial savings. The invention may also be used for other heart treatments, for example, for thermal or microwave irradiation treatments.

SHORT DESCRIPTION OF THE DRAWINGS

FIG. 1 is a cross-sectional view of the distal end of a heart catheter; and

FIG. 2 shows the end of the catheter with sensors and light transmitting fiber extended.

DESCRIPTION OF THE PREFERRED EMBODIMENT

The distal end of a heart catheter as shown in cross-section in FIG. 1 consists of a plastic hose 1 which is provided with an end piece or sonde 2 forming a first electrode, with part of which the hose 1 is engaged for mounting purposes. A second electrode 3 in the form of a ring structure extends around and engages the hose at a certain distance from the first electrode. The first and second electrodes 2 and 3 are electrically insulated from one another and connected to cables 4 and 5 for transmitting their potentials to a computer or control unit, not shown in the drawing.

A light transmitting fiber 6 at least partially provided with surface insulation 7 is preferably coaxially supported within the hose 1 such that it is axially movable in the interior 13 of the hose 1. For axially moving the fiber there is provided a mechanical push-pull device which may simply consist of a slide member 8 disposed in the hose 1 so as to be slidable along its interior wall 13 or along the interior wall 14 of the first electrode 2 and having sensors 9 mounted thereon for movement therewith. The light transmitting fiber 6 is connected to the slide member 8 by way of an insulating material ring 10 which is tightly disposed on the fiber 6 so as to engage an inwardly projecting collar of the slide member 8 between the insulating material sleeve 7 and the ring 10. The slide member 8 may of course be connected to the fiber 6 in another manner, for example, simply by cementing the slide member 8 onto the sleeve 7. Axial movements of the slide member 8 are initiated either by way of the fiber and fiber sleeve and a pull string or by way of a push-pull cable 11 alone.

The sensors 9 are preferably mounted on the cylinder or on the face surfaces 12 of the piston 8. They consist of metal wires which are formed and pretensioned so as to project outwardly when extended forwardly out of the electrode 2 with which however they remain in electrical contact.

The pretension and the length of the sensors 9 are so selected that, on one hand, they center the tip 15 of the fiber 6 and, on the other hand, are capable of spreading outwardly when, under the guidance of inclined guide bores 16 extending through the first electrode 2, the slide member 8 is moved forwardly to the forward end positions of the fiber 6 and the sensors 9 as shown in FIG. 2. The free ends of the sensors 9 then project somewhat beyond the end tip 15 of the fiber such that the end tip 15 will not come into contact with the endocardium. The tips of the sensors 9 however become anchored in the endocardium during the advance movement and as a result provide for firm location of the sonde 2 and the fiber 6. Forward movement of the slide member is limited by the stop member 17.

During an irradiation procedure during which the sensors 9 and the fiber 6 are extended (position of FIG. 2) a physiological solution 19 (i.e., NaCl solution) is introduced through the space between the fiber 6 or rather the insulation coating 7 and the interior wall 13 of the hose 1 which flows past the piston 8, that is, through channels 18 in the slide member toward the fiber tip 15 out of the electrode 2. In the process the solution cools the fiber tip 15 and keeps the space within the electrode 2 and also the area around the fiber 6 all the way up to the tissue to be irradiated transparent and clean and free of blood.

In this manner the blood is kept away from the device and the formation of blood clots in the radiation exposed areas is prevented.

What is claimed is:

1. A heart catheter comprising a hose having a distal end forming a sonde including an electrode structure means for locating pathological areas, a light transmitting fiber disposed in said hose so as to extend axially therethrough and being axially movable therein, said light transmitting fiber having a tip for the irradiation of said pathological areas, said electrode structure means including electrical sensors mounted on a slide member axially movably disposed in the distal end of said hose and said light transmitting fiber having an insulation sleeve to which said slide member is connected, a mechanical push-pull structure operably associated with said slide member for axial advance of said electrical sensors in unison with said fiber thereby rendering said electrical sensors retractable into and extendable from the distal end of said hose while maintaining a predetermined distance between said fiber tip and the front end of said electrical sensors which are adapted to engage tissue in said pathological areas for securing the position of said sonde relative to said tissue, said fiber being spaced from said hose so as to provide a passage space between said fiber and the inner wall of said hose adapted to conduct a physiological solution through the hose to the distal end thereof for discharge therefrom around the end tip of said fiber when said fiber and said electrical sensors are extended thereby forming a solution path in front of said fiber tip to said tissue through which laser light supplied to said fiber is conductable to said tissue while said fiber tip remains at said predetermined distance therefrom.

2. A heart catheter according to claim 1, wherein said sensors are preset in shape so that they spread outwardly when extended from the distal end of said hose.

3. A heart catheter according to claim 1, wherein said sensors extend through bores formed in said electrode structure at the distal end of said hose.

4. A heart catheter according to claim 1, wherein a stop member is provided so as to project into the path of movement of said sensors so as to limit the axial movement of said sensors.

* * * * *